United States Patent
Fujiwara et al.

(10) Patent No.: US 8,153,161 B2
(45) Date of Patent: Apr. 10, 2012

(54) MEDICAMENT-CONTAINING PARTICLE AND A SOLID PREPARATION CONTAINING THE PARTICLE

(75) Inventors: Keiichi Fujiwara, Ibaraki (JP); Kiyomi Sogo, Osaka (JP); Shizuo Okamoto, Osaka (JP); Koichiro Shibamori, Osaka (JP); Norihito Shimono, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 194 days.

(21) Appl. No.: 10/582,174

(22) PCT Filed: Dec. 7, 2004

(86) PCT No.: PCT/JP2004/018204
§ 371 (c)(1), (2), (4) Date: Jun. 8, 2006

(87) PCT Pub. No.: WO2005/055989
PCT Pub. Date: Jun. 23, 2005

(65) Prior Publication Data
US 2007/0148230 A1 Jun. 28, 2007

(30) Foreign Application Priority Data
Dec. 9, 2003 (JP) .................... 2003-410961

(51) Int. Cl.
*A61K 9/50* (2006.01)
*A61K 9/20* (2006.01)
(52) U.S. Cl. ...................... 424/499; 424/465
(58) Field of Classification Search ............... 424/465, 424/499
See application file for complete search history.

(56) References Cited

U.S. PATENT DOCUMENTS

| 4,870,074 | A | | 9/1989 | Kon et al. |
| 5,580,576 | A | | 12/1996 | Veronesi et al. |
| 5,607,697 | A | * | 3/1997 | Alkire et al. ............... 424/495 |
| 5,976,577 | A | | 11/1999 | Green et al. |
| 6,132,771 | A | * | 10/2000 | Depui et al. ............... 424/468 |
| 6,235,947 | B1 | * | 5/2001 | Yoshinari et al. ........... 568/852 |

(Continued)

FOREIGN PATENT DOCUMENTS
CN 1359680 A 7/2002
(Continued)

OTHER PUBLICATIONS

MIMS, Gasmotin® [film-coated tab], printed from http://www.mims.com/Page.aspx?menuid=mng&brief=false&name=Gasmotin%20film-coated%20tab&h=Gasmotin%20film-coated%20tab&CTRY=TH&sm=1 on May 28, 2010, 7 pages.*

(Continued)

*Primary Examiner* — Sreeni Padmanabhan
*Assistant Examiner* — Gigi Huang
(74) *Attorney, Agent, or Firm* — Birch, Stewart, Kolasch & Birch, LLP

(57) ABSTRACT

The invention provides a medicament-containing particle wherein an unpleasant taste of the medicament is alleviated, which is obtainable by mixing and granulating the following ingredients: (1) the medicament with an unpleasant taste, (2) methylcellulose and (3) mannitol; and a solid preparation including the particle. The invention can make an unpleasant taste of the medicament alleviated and furthermore when the formulation including the particle is administered, the unpleasant taste can be masked and the formulation has a good dissolvability in gastrointestinal tract.

21 Claims, 1 Drawing Sheet

U.S. PATENT DOCUMENTS

| | | | |
|---|---|---|---|
| 6,368,625 B1 * | 4/2002 | Siebert et al. | 424/466 |
| 6,413,541 B1 * | 7/2002 | Shirai et al. | 424/435 |
| 6,517,870 B1 * | 2/2003 | Nishii et al. | 424/489 |
| 2001/0055611 A1 | 12/2001 | Green et al. | |
| 2004/0081691 A1 * | 4/2004 | Debregeas et al. | 424/465 |
| 2004/0109890 A1 | 6/2004 | Sugimoto et al. | |
| 2004/0213839 A1 | 10/2004 | Favara et al. | |

FOREIGN PATENT DOCUMENTS

| | | |
|---|---|---|
| EP | 0 076 515 A1 | 4/1983 |
| EP | 1 120 120 A1 | 8/2000 |
| EP | 1 125 576 A1 | 8/2001 |
| EP | 1 295 575 A1 | 3/2003 |
| JP | 56-164122 A | 12/1981 |
| JP | 58145 A | 4/1983 |
| JP | 5-17360 A | 1/1993 |
| JP | 6-40916 A | 2/1994 |
| JP | 8-40885 A | 2/1996 |
| JP | 11-349475 A | 12/1999 |
| JP | 2001-39861 A | 2/2001 |
| JP | 2002-512953 A | 5/2002 |
| JP | 2004-26675 A | 1/2004 |
| JP | 2004-161701 A | 6/2004 |
| WO | WO-99/2140 A1 | 1/1999 |
| WO | WO-02/062320 A1 | 8/2002 |
| WO | WO-02/064119 A1 | 8/2002 |
| WO | WO-02/076462 A1 | 10/2002 |
| WO | WO-2004/066913 A2 | 8/2004 |

OTHER PUBLICATIONS

Chinese Office Action dated Jun. 27, 2008.

* cited by examiner

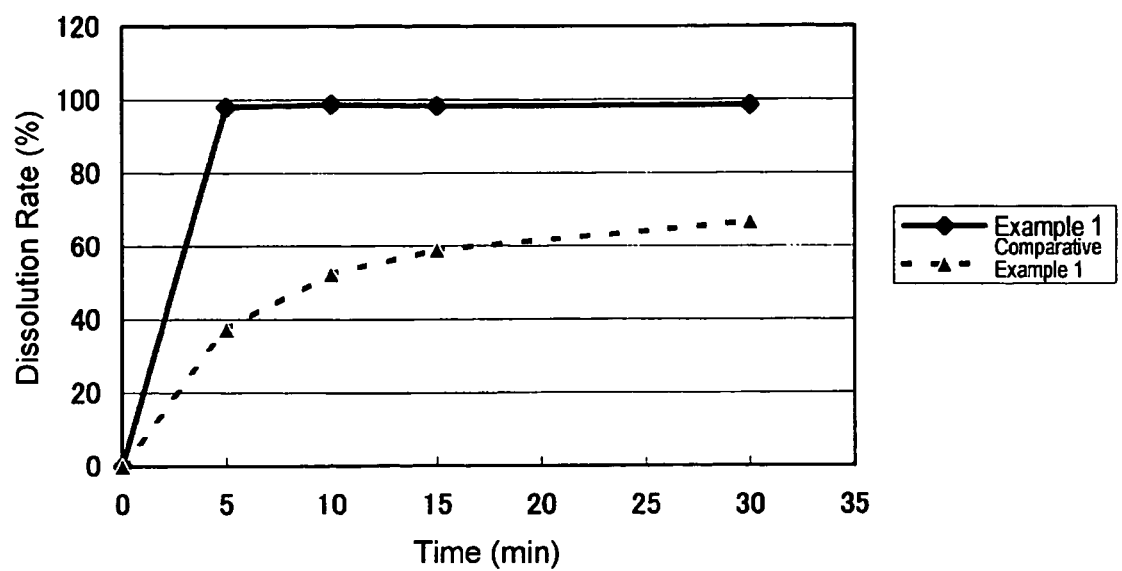

MEDICAMENT-CONTAINING PARTICLE AND A SOLID PREPARATION CONTAINING THE PARTICLE

TECHNICAL FIELD

The present invention relates to a medicament-containing particle and a solid preparation containing the particle. More particularly, it relates to a medicament-containing particle wherein an unpleasant taste of the medicament having the unpleasant taste is alleviated in buccal cavity, and "a solid preparation containing the particle" which does not substantially induce an unpleasant taste of the medicament and has a good dissolvability in gastrointestinal tract.

BACKGROUND ART

A lot of medicaments contained in pharmaceutical products induce an unpleasant taste such as bitter taste, astringent taste and pungent taste when the pharmaceutical product is orally administered. In case that a medicament has such an unpleasant taste, it is very difficult for a patient to take a pharmaceutical product containing the medicament. A big problem to be solved for the preparation thereof is how to mask such an unpleasant taste of the medicament in the preparation. In order to solve this problem, i.e. in order to mask the unpleasant taste of the medicament when the medicament is orally administered, a sweetener or a flavor has hitherto usually been used as an additive, but sometimes an increased amount of the sweetener is required to fully mask a bitter taste. Alternatively, a coating of a medicament or a medicament-containing granule, and so on has been applied with a water-insoluble polymer base such as ethyl cellulose. With respect to this method, however, in order to more effectively depress an unpleasant taste of the medicament, it is necessary to coat it in more coating amount. As a result, the coating may affect a releasing amount of the medicament transferred into gastrointestinal tract and the desired release of the medicament can not be obtained, which is another problem.

For example, in case of an intrabuccally rapidly disintegrating tablet, it has been desired to produce a tablet having good disintegrability in buccal cavity and good dissolubility in gastrointestinal tract. However, when the intrabuccally rapidly disintegrating tablet contains a medicament having an unpleasant taste, it is difficult to simultaneously satisfy above the two conditions of rapid disintegrability in buccal cavity and alleviation of an unpleasant taste in buccal cavity because these conditions are inconsistent to each other, and it is furthermore difficult to simultaneously satisfy the condition of alleviating an unpleasant taste in buccal cavity and the condition of good dissolubility in gastrointestinal tract, because these conditions are also inconsistent to each other. Furthermore, it is also difficult to simultaneously satisfy all these conditions mentioned above.

The present inventors have studied for obtaining the desired preparation, and during which they have given in attention to previously granulate the medicament with the other ingredients and further to use a water-soluble polymer in the granulating procedure. It is already known that a particle (or granule) obtained by granulating a medicament is formulated into a drug preparation, for example, WO 2002/002083 discloses "a quick disintegrating tablet in buccal cavity, said quick disintegrating tablet comprising: spray-dried drug-containing particles, wherein each particle comprises a bitter tasting drug and/or a drug of inferior fluidity and a pharmaceutical preparation carrier, wherein each particle has a mean diameter of approximately 50 μm to approximately 250 μm and an apparent specific gravity of approximately 0.5 to approximately 1.2, and a saccharide." The pharmaceutical preparation carrier in this reference includes water-insoluble polymers, gastrosoluble polymers, enterosoluble polymers, wax-like substances and saccharides as an example, in detail, the reference discloses a working example using a water-insoluble polymer. Thus it is disclosed in the patent gazette that such "a particle-form containing a medicament" which includes a water-insoluble polymer such as ethyl-cellulose may make a bitter thereof masked. In addition, it is disclosed in the patent gazette as "the fluidity of a drug that is not bitter tasting can be improved by the present invention, and in this case, the above-mentioned polymer substances, such as water-insoluble polymer, gastrosoluble polymer, enterosoluble polymer, etc., and wax-like substances, etc., a water soluble polymer, saccharide, etc., can be used as the above-mentioned carrier. Examples of the water-soluble polymers as the carrier are hydroxypropyl cellulose, hydroxypropyl methyl cellulose, polyvinyl pyrrolidone, polyvinyl alcohol, etc." Thus, this publication suggests that even if a medicament-containing particle which includes the medicament with a bitter taste and a water-soluble polymer is produced, the bitter taste thereof cannot be masked.

In addition, JP-A-2001-039861 discloses, for example, "a tablet obtained by mixing (1) (a) a granule in which a medicament is included in a water-soluble polymer matrix or a wax matrix and/or (b) a granule prepared by coating a medicament-containing granule with a water-soluble polymer or a water-insoluble polymer film, with (2) an excipient, (3) adding a solvent thereto, kneading the resultant mixture, and (4) placing the kneaded mixture in a mold, and then molding the kneaded mixture to form a tablet." In the reference, hydroxypropyl cellulose, hydroxypropylmethylcellulose, methylcellulose, sodium carboxymethylcellulose, and polyvinylpyrrolidone, polyvinyl alcohol are exemplified as a water-soluble polymer. However, the granule mentioned in patent the gazette has a feature that a medicament can be gradually released in water or in gastrointestinal tract. Accordingly, the problem of the reference is contrary to that of the present invention.

In addition, WO 2000/024379 discloses a preparation method of drug-containing spherical fine particles that are useful in the production of easily-swallowed, controlled-release preparations. In detail, it discloses that "a preparation method of drug-containing spherical fine particles having a mean particle size of 200 μm or less comprising: adding a binder solution to a mixture containing an excipient powder having the property of retaining a solvent and a drug powder, and granulating by high-speed mixing." In the reference, celluloses such as microcrystalline cellulose, methylcellulose, carmellose sodium, carmellose calcium, and low-substituted hydroxypropyl cellulose, and various starches are exemplified as an excipient having the property of retaining a solvent. However, the patent gazette discloses neither any masking of a bitter taste of a medicament nor any combination of a medicament having an unpleasant taste, methylcellulose and mannitol as in the present invention mentioned hereinafter.

In addition, JP-A-2000-191518 discloses that "a method for preparing an intrabuccally quickly disintegrating tablet, which comprises dissolving a difficultly soluble pharmaceutical agent together with a surfactant and/or a water-soluble polymer in an organic solvent or an water-containing organic solvent, coating an excipient with the solution or granulating the excipient with the solution to obtain molded products, mixing a saccharide with them, adding an organic solvent, water or an water-containing organic solvent thereto, followed by kneading, and subjecting it to a compression-molding." However, the patent gazette discloses the improvement of dissolubility of a difficultly soluble medicament, but does not disclose a masking of a bitter taste. Additionally, the example section discloses examples only using surfactants, but does not disclose any example using a water-soluble polymer. Furthermore, the patent gazette does not disclose anything about a combination of a medicament with an unpleasant taste, methylcellulose and mannitol as the present invention discloses.

DISCLOSURE OF INVENTION

Problem to be Solved by the Invention

As mentioned above, with regard to a solid preparation containing a medicament with an unpleasant taste, it had been difficult to mask an unpleasant taste of a medicament and carry out a rapid dissolution in gastrointestinal tract by now.

Means to Solve the Problem

Under such situation, the present inventors have found that a bitter taste of a medicament in buccal cavity could be alleviated by preparing a medicament-containing particle with methylcellulose which has been used as a conventional base for sustained release or for coating among various water-soluble polymers and a specific sugar alcohol, and furthermore that a rapid dissolution in gastrointestinal tract and a masking of an unpleasant taste could simultaneously be carried out when taking a preparation containing the particle; thereby they have succeeded in resolving the above problem, then have accomplished the present invention. Furthermore, with regard to an intrabuccally rapidly disintegrating preparation, they have found that the present invention make the drug preparation intrabuccally rapidly integrated and also make a bitter taste of the intrabuccal medicament alleviated.

The present invention provides various embodiments of the invention as mentioned below.

[1] A medicament-containing particle wherein an unpleasant taste of the medicament is alleviated, which is obtainable by mixing and granulating the following ingredients:
(1) the medicament with an unpleasant taste,
(2) methylcellulose, and
(3) mannitol.

[2] The medicament-containing particle according to the above [1] wherein the amount of the methylcellulose is about 0.05 to about 10 parts by weight per 1 part by weight of the medicament with an unpleasant taste.

[3] The medicament-containing particle according to the above [1] wherein the amount of the methylcellulose is about 0.15 to about 7 parts by weight per 1 part by weight of the medicament with an unpleasant taste.

[4] The medicament-containing particle according to the above [1] wherein the amount of the methylcellulose is about 0.8 to about 5 parts by weight per 1 part by weight of the medicament with an unpleasant taste.

[5] The medicament-containing particle according to any one of the above [1]-[4] wherein the amount of the mannitol is about 0.3 to about 50 parts by weight per 1 part by weight of the methylcellulose.

[6] The medicament-containing particle according to any one of the above [1]-[4] wherein the amount of the mannitol is about 0.5 to about 12 parts by weight per 1 part by weight of the methylcellulose.

[7] The medicament-containing particle according to any one of the above [1]-[4] wherein the amount of the mannitol is about 0.7 to about 7.5 parts by weight per 1 part by weight of the methylcellulose.

[8] The medicament-containing particle according to any one of the above [1]-[7] wherein the mannitol is D-mannitol.

[9] The medicament-containing particle according to any one of the above [1]-[8] wherein the medicament with an unpleasant taste is 4-amino-5-chloro-2-ethoxy-N-[[4-(4-fluorobenzyl)-2-morpholinyl]methyl]benzamide or a pharmaceutically acceptable salt thereof.

[10] The medicament-containing particle according to the above [1], which is obtainable by mixing and granulating the following ingredients:
(1) (±)-4-amino-5-chloro-2-ethoxy-N-[[4-(4-fluorobenzyl)-2-morpholinyl]methyl]benzamide citrate dihydrate as a medicament,
(2) methylcellulose, and
(3) D-mannitol,
wherein the amount of the methylcellulose is about 0.15 to about 7 parts by weight per 1 part by weight of (±)-4-amino-5-chloro-2-ethoxy-N-[[4-(4-fluorobenzyl)-2-morpholinyl]methyl]benzamide citrate, and
the amount of the D-mannitol is about 0.5 to about 12 parts by weight per 1 part by weight of the methylcellulose.

[11] A solid preparation comprising the medicament-containing particle set forth in any one of the above [1]-[10] and other ingredients for pharmaceutical preparation.

[12] The solid preparation according to the above [11] which is a tablet-like preparation or a granule-like preparation.

[13] The solid preparation according to the above [12] wherein the tablet-like preparation is in the form of a tablet or a pill.

[14] The solid preparation according to the above [12] wherein the granule-like preparation is in the form of a granule, a fine granule or a powder.

[15] The solid preparation according to any one of the above [11]-[14] which is an intrabuccally rapidly disintegrating preparation.

[16] The solid preparation according to the above [15] wherein the intrabuccally rapidly disintegrating preparation is in the form of a tablet.

[17] The solid preparation according to the above [15] wherein the intrabuccally rapidly disintegrating preparation is a granule-like preparation.

[18] The intrabuccally rapidly disintegrating preparation set forth in any one of the above [15]-[17] which is characterized by the following properties:
(i) disintegrating within 40 seconds on a tongue of a healthy adult with his mouth closed and without chewing,
(ii) dissolving at a substantial dissolution rate of 85% or more after 15 minutes according to the dissolution test described in the Japanese Pharmacopoeia XIV [using Method 2 (50 rpm) for tablets or Method 1 (50 rpm) for granule-like preparation, resolution medium: 900 mL of water], and
(iii) not substantially feeling an unpleasant taste on setting the preparation in buccal cavity.

[19] A composition for preparing the intrabuccally rapidly disintegrating preparation set forth in the above [15], which comprises
a medicament-containing particle wherein an unpleasant taste of the medicament is alleviated, which is obtainable by mixing and granulating the medicament with an unpleasant taste, methylcellulose and mannitol;
an excipient; and
a disintegrator.

[20] A process for preparing a medicament-containing particle wherein an unpleasant taste of the medicament is alleviated, which is obtainable by mixing (1) the medicament with an unpleasant taste, (2) methylcellulose and (3) mannitol, and granulating the mixture with water or a water-containing solvent.

[21] A commercial package which comprises the solid preparation set forth in the above [11] comprising 4-amino-5-chloro-2-ethoxy-N-[[4-(4-fluorobenzyl)-2-morpholinyl]-methyl]benzamide or a pharmaceutically acceptable salt thereof as a medicament with an unpleasant taste; and a written matter as to the solid preparation,
including a description on the outside of the package or the written matter inside the package which intends that the solid preparation can/should be used for promoting gastrointestinal motility, improving postgastrectomy condition, or preventing/treating gastroesophageal reflux disease (GERD).

BRIEF DESCRIPTION OF DRAWINGS

FIG. 1 shows results of the dissolution test using each tablet in Example 1 and Comparative Example 1.

BEST MODE FOR CARRYING OUT THE INVENTION

The "average particle size" used in the present claims and specification, unless otherwise indicated, is denoted as a value measured, for example, by means of a laser diffraction particle size analyzer (HELOS & RODOS) (SYMPATEC Inc.).

The "per 1 part by weight of the medicament" used in the present claims and specification is based on a form of "pharmaceutically active ingredient" which is generally used in pharmaceutical field. Regarding a medicament as a salt form, it is based on 1 part by weight of the salt thereof. However, when a medicament has crystal water, it is the residual amount by subtracting the amount of crystal water therefrom.

The medicament-containing particle of the invention is essentially a medicament-containing particle wherein an unpleasant taste of the medicament is alleviated, which is obtainable by mixing and granulating the following ingredients:
(1) the medicament with an unpleasant taste,
(2) methylcellulose, and
(3) mannitol;
and each of the ingredients is explained as follows.
(1) A Medicament with an Unpleasant Taste There are no special restriction to the "medicament with an unpleasant taste" used in the present invention as long as it is a one that is used for treating or preventing a disease as a pharmaceutically active ingredient, and it is a one with an unpleasant taste such as bitter taste, astringent taste and pungent taste. The medicaments include antipyretic-analgesic-antiinflammatory drugs, quinolone antibacterial agents, antibiotics, antitumor agents, gastrointestinal agents, antidiarrheals, antidepressants, antiepileptics, antihypertensives and so on. The examples of the medicaments include mosapride citrate shown below, quinine sulfate, morphine sulfate, morphine hydrochloride, caffeine, ethenzamide, codeine phosphate, dihydrocodeine phosphate, berberine chloride, acrinol, zonisamide, loperamide hydrochloride, gatifloxacin, sparfloxacin, alacepril, clarithromycin and so on. As mentioned above, the medicament may be in the form of a salt-free or a salt. Additionally it may be in the form of a hydrate.

Especially, the preferable medicament with an unpleasant taste which is adapted for the present invention is 4-amino-5-chloro-2-ethoxy-N-[[4-(4-fluorobenzyl)-2-morpholinyl] methyl]benzamide or a pharmaceutically acceptable salt thereof, which is shown in the following formula. The compound (or the acid addition salt or the hydrate thereof) is a selective agonist of serotonin 4 receptor, which can exhibit an acceptable effect promoting gastrointestinal motility (U.S. Pat. No. 4,870,074). The compound can be prepared according to, for example, the method described in U.S. Pat. No. 4,870,074 or a modified method thereof. In addition, the compound is also useful as a medicament for treating gastroesophageal reflux disease, postgastrectomy syndrome, or the other gastrointestinal symptom.

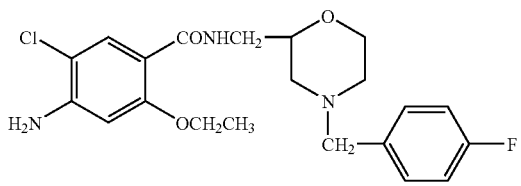

The citrate.dihydrate of the above racemic mixture (hereinafter, occasionally referred to as "mosapride") have already been practically used for improving gastrointestinal symptom accompanied with chronic gastritis, and tablets containing 2.5 mg or 5 mg of mosapride citrate (anhydride) (1.72 mg or 3.44 mg of mosapride) have been marketed under the trade name "Gasmotin" in Japan. These tablets are sold as a film-coating tablet since mosapride is a bitter medicament.

As another solid preparation containing mosapride; U.S. Pat. No. 4,870,074 discloses a solid preparation containing mosapride citrate, corn starch, lactose, crystalline cellulose, hydroxypropyl cellulose, light anhydrous silicic acid and magnesium stearate in Example 245.

In addition, WO 2004/066913 discloses a solid preparation (except orally disintegrating tablets) free of film coating, which is substantially free of light anhydrous silicic acid and which comprises mosapride or a salt thereof.

On the other hand, as an intrabuccally rapidly disintegrating tablet containing mosapride citrate, JP-A-1999-349475 discloses a process for preparing an intrabuccally rapidly disintegrating tablet containing mosapride citrate which comprises leaving tablets containing amorphous lactose and molded under a low pressure under the relative humidity of about 60% to about 90%, and converting the amorphous lactose into the crystalline lactose. Furthermore, U.S. Pat. No. 6,413,541 discloses a process for preparing an intrabuccally rapidly disintegrating tablet containing mosapride citrate which comprises the following Steps (a), (b) and (c), wherein a medicament is mixed before granulation or tabletting (b):
(a) a step of dissolving at least one saccharide having a high solubility in water and at least one water-soluble binder in water alone or in water and an alcohol; (b) a step of mixing the solution obtained in the above Step (a) with at least one excipient, granulating, drying and tabletting the mixture under a low compression pressure; (c) a step of aging the tablets obtained in Step (b).

However, any gazettes do not disclose any description about a particle containing mosapride citrate.

4-Amino-5-chloro-2-ethoxy-N-[[4-(4-fluorobenzyl)-2-morpholinyl]methyl]benzamide may be in the form of racemic mixture or in either enantiomeric form thereof, however, the racemic compound thereof (i.e. "mosapride") is preferable. In addition, mosapride may be in a free form thereof or in the form of a pharmaceutically acceptable salt thereof. The preferable salt is an acid addition salt. The acid addition salt with an organic acid includes, for example, formate, acetate, lactate, adipate, citrate, tartrate, fumarate, methanesulfonate, maleate, etc.; and the acid addition salt with an inorganic acid includes, for example, hydrochloride, sulfate, nitrate, phosphate, etc. Especially, citrate is preferable among them. Furthermore, mosapride or a pharmaceutically acceptable salt thereof may exist in the form of a solvate, a hydrate, or a non-hydrate. A hydrate of citrate is preferable, especially the citrate dihydrate thereof is more preferable.

(2) Methylcellulose

The "methylcellulose" formulated in the medicament-containing particle of the present invention has an action masking an unpleasant taste of the medicament by the specific combination with mannitol. It had not been thought that methylcellulose is useful for masking an unpleasant taste as mentioned the following gazettes. For example, JP-A-56-164122 discloses that it was failed to mask a bitter taste with methylcellulose (the reference formulation C in JP-A-56-164122). Additionally, WO 2002/002083 also discloses it was failed to alleviate a bitter taste of a medicament having a bitter taste by a granulation with a water-soluble polymer as mentioned above.

In the present invention, it has been found that the combination of mannitol with methylcellulose which is selected among a lot of kinds of water-soluble polymers can provide the desired effect. In other words, the desired effect could not be obtained when using the other water-soluble polymer which is used for known granulation, such as hydroxypropyl cellulose, hydroxypropylmethylcellulose, pullulan, polyvinylpyrrolidone and polyvinyl alcohol; however, the desired effect could be exhibited when using methylcellulose (see below, Comparative Example).

The amount of the methylcellulose may be about 0.05 to about 10 parts by weight, preferably about 0.15 to about 7 parts by weight, more preferably about 0.8 to about 5 parts by weight, per 1 part by weight of the medicament.

(3) Mannitol

Mannitol is one of essential ingredients in the medicament-containing particle of the present invention. The sugar or sugar alcohol which can exhibit the desired effect in combination with methylcellulose is the above-mentioned mannitol. In other words, the desired effect could not be obtained by using the other sugars or sugar alcohols, however, has been incipiently accomplished by using mannitol (see below, Comparative Example). The preferable mannitol is D-mannitol.

The amount of the mannitol may be about 0.3 to about 50 parts by weight, preferably about 0.5 to about 12 parts by weight, more preferably about 0.7 to about 7.5 parts by weight, per 1 part by weight of methylcellulose.

Medicament-Containing Particle

The particles are prepared by mixing and granulating the above ingredients (1)-(3). In more detail, they are obtainable by mixing the above ingredients (1)-(3) and granulating the mixture with water or water-containing solvent. The method include a method for mixing the ingredients and then granulating the mixture with water or water-containing solvent; or a method for dissolving a part of methylcellulose in water, adding the solution to the mixture and then granulating it. Furthermore, the method also includes a method for mixing the ingredients, adding water or water-containing solvent which includes the other conventional binder within the range of the amount that could not influence the effect of the invention, and then granulating it. The method of the granulation includes a conventional method such as an agitation granulation method, an extrusion granulation method, a fluidized bed granulation method, a dry granulation method and the like.

The average particle size of a medicament-containing particle may be about 500 μm or less, for example, about 5 to about 500 μm, preferably about 10 to about 400 μm, more preferably about 10 to about 300 μm. The average particle size thereof can be determined under a consideration of the feeling in buccal cavity when administered and the dissolvability as well as the effect masking an unpleasant taste.

In the medicament-containing particle of the invention, the amount of the methylcellulose may be about 0.05 to about 10 parts by weight per 1 part by weight of the medicament with an unpleasant taste. Preferably, the amount of the methylcellulose in the medicament-containing particle may be about 0.15 to about 7 parts by weight per 1 part by weight of the medicament with an unpleasant taste. More preferably, the amount of the methylcellulose formulated in the medicament-containing particle may be about 0.8 to about 5 parts by weight per 1 part by weight of the medicament with an unpleasant taste.

In addition, the amount of the mannitol in the medicament-containing particle may be about 0.3 to about 50 parts by weight per 1 part by weight of the methylcellulose. Preferably, the amount of the mannitol formulated in the medicament-containing particle may be about 0.5 to about 12 parts by weight per 1 part by weight of the methylcellulose. More preferably, the amount of the mannitol formulated in the medicament-containing particle may be about 0.7 to about 7.5 parts by weight per 1 part by weight of the methylcellulose.

The "medicament-containing particle" of the present invention is intended to mean that methylcellulose does not overall covers over the medicament, but a part of the medicament can exist on the surface of the particle. The medicament-containing particle thus obtained can make the unpleasant taste of the medicament itself alleviated.

The medicament-containing particle of the invention may further include corrigents, fluidization agents, stabilizers, surfactants, disintegrants, coloring agents, etc in the particle. These ingredients are exemplified in the following solid preparation, which can be used as the above ingredients.

Solid Preparation of the Present Invention

Using the medicament-containing particle of the present invention, a solid preparation can be prepared. An applicable formulation thereof is, for example, a tablet-like preparation or a granule-like preparation. The tablet-like preparation includes, for example, tablets and pills; and the granule-like preparation includes, for example, granules, fine granules and powders. In addition, the solid preparation may include an intrabuccally rapidly disintegrating preparation which includes tablets (intrabuccally rapidly disintegrating tablets) and a granule-like preparation (intrabuccally rapidly disintegrating granules or intrabuccally rapidly disintegrating powders).

In addition to a medicament-containing particle, the solid preparation of the invention may contain a pharmaceutically acceptable ingredient for pharmaceutical preparation which is ordinarily used for preparing a pharmaceutical solid preparation as long as there is no particular inconvenience. As to the "ingredient for pharmaceutical preparation", any ingredients which give no bad effect on the preparation and have a necessity to be formulated are available, which include, for example, an excipient, a binder, a lubricant, a disintegrant and the like.

Examples of the excipients are lactose, sucrose, D-mannitol, starch, crystalline cellulose, erythritol, trehalose, anhydrous calcium hydrogen phosphate, calcium sulfate and the like. Examples of the binders are gum arabic, starch, hydroxypropyl cellulose, hydroxypropyl-methylcellulose, polyvinylalcohol, pullulan, gelatin, ethylcellulose, methylcellulose, carmellose sodium, dextrin, polyvinylpyrrolidone and the like.

Examples of the lubricants are stearic acid and a metallic stearate such as magnesium stearate and calcium stearate, talc, colloidal silica, a sucrose fatty acid ester, talc, hydrogenated oil, polyethylene glycol and the like; and examples of the disintegrants are low-substituted hydroxypropyl cellulose, croscarmellose sodium, carmellose calcium, crospovidone, sodium carboxymethyl starch, partly pregelatinized starch and the like.

When necessary, stabilizers (disodium edetate, tocopherol, L-ascorbic acid, L-cysteine, sulfite, etc.), fluidization agents (light anhydrous silicic acid, magnesium aluminometasilicate, etc.), surfactants (sodium lauryl sulfate, polysorbates, etc.), preservatives, coloring agents (food colorant, iron sesquioxide, carmine, etc.), flavors (various fruit-flavors such as strawberry flavor, yogurt, mint, menthol, etc.), corrigents and the like may be added.

The corrigents include neotame, thaumatin, aspartame, stevia, saccharin sodium, sodium glutamate, etc., which may be used as a single or a mixture of 2 or more kinds of the corrigents. For example, two kinds of corrigents, one exhibits a rapid expression of flavor and the other exhibits a slow expression of flavor, may be combined. The rapidly-expressed corrigent includes neotame, sodium glutamate, saccharin sodium, etc., and the slowly-expressed corrigent includes thaumatin, stevia, etc.

The solid preparation of the present invention can be prepared in a conventional process of the pharmaceutical field. For example, the medicament-containing particle of the present invention can be homogeneously mixed with the above-mentioned ingredients and then the mixture can be processed into a preparation by a known method. The mixture can be processed into various solid preparations for oral administration such as tablets, pills, powders, granules and fine granules. In the case of tablets, for example, to a medicament-containing particle, an excipient, a disintegrant and so on are added, mixed and a binder is added to the mixture and then the obtained mixture is granulated to give granules. And a lubricant is added to the granules and the resulting mixture can be compressed to give tablets. Alternatively, a medicament-containing particle and ingredients for pharmaceutical preparation such as an excipient, a disintegrant and so on may be mixed in a blender and then compressed; or the mixture of the ingredients for pharmaceutical preparation may be granulated, and then mixed with a medicament-containing particle, and compressed. In addition, the granules can be prepared by a fluidized bed granulation method or an agitation granulation method which is almost the same method as the case of the tablets. The powders or other can be also prepared in a similar manner.

In the present invention, the medicament-containing particle may be also applied to an intrabuccally rapidly disintegrating preparation. The "intrabuccally rapidly disintegrating preparation" of the present invention means that the preparation can be integrated mainly with intrabuccal saliva within usually 40 seconds, preferably 35 seconds without water for taking a preparation. The intrabuccally rapidly disintegrating tablet generally contains a lubricant, wherein the lubricant may be included inside the tablet or localized on the surface of the tablet. The tablet wherein a lubricant is localized on the surface thereof can be prepared, for example, by mixing a medicament-containing particle of the present invention with the other ingredients for pharmaceutical preparation such as the appropriate excipient and disintegrant mentioned above and compressing the mixture by means of a tableting machine wherein a lubricant adheres onto punches and dies thereof.

The "lubricant adheres onto punches and dies thereof" mentioned above may be carried out manually, but preferably mechanically. Such the method is called "an external lubricating compression method." The means and the apparatuses which make the above-mentioned external lubricating compression method possible include, for example, a means or an apparatus for supplying externally a lubricant and a means for recovering the external lubricant as disclosed in JP-A-2001-205493 and JP-A-2001-293599. For example, in compressing a powder which comprises a medicament-containing particle, an excipient, a disintegrant and the other optional ingredients for pharmaceutical preparation, the tablet which contains a lubricant in 0.01-0.5% by weight can be continuously formed by a tableting machine equipped with an external lubricant supplying apparatus and an external lubricant recovering apparatus wherein the lubricant is continuously pre-sprayed to adhere onto the punches and the dies of the tableting machine and the unused surplus of lubricant is continuously recovered.

The solid preparation of the present invention thus obtained can let a person not feel an unpleasant taste of a medicament in his buccal cavity, and exhibits a good dissolubility in gastrointestinal tract. And the substantial dissolution rate thereof after 15 minutes is about 85% or more via the dissolution test of the Japanese Pharmacopoeia XIV [37° C., resolution medium: 900 mL of water, using Method 2 (50 rpm) for a tablet-like preparation, Method 1 (50 rpm) for a granule-like preparation]. The dissolution rate of the dissolution test can be determined with the test sample by a conventional assay such as spectrophotometry and liquid chromatography.

Additionally, the solid preparation of the invention is packaged with a written matter on which the information of the preparation is described and the packages are commercialized. The written matter may be included on the outside of the package or in the instruction sheet inside the package. The "information of solid preparation" used herein can include as an example an information that the solid preparation can/should be used for promoting gastrointestinal motility, improving postgastrectomy condition, or preventing/treating gastroesophageal reflux disease (GERD) when the medicament is (±)4-amino-5-chloro-2-ethoxy-N-[[4-(4-fluorobenzyl)-2-morpholinyl]methyl]-benzamide, or a pharmaceutically acceptable salt thereof.

EXAMPLE

The present invention is illustrated in more detail by the following Examples, but it should not be construed to be limited thereto. In the following Examples, the intrabuccally rapidly disintegrating tablets are produced with a rotary type tableting machine (Kikusui Seisakusho Ltd., Type Collect 19 K) equipped with an external lubricant spraying system which has an external lubricant supplying function and a recovering function (Kikusui Seisakusho Ltd., ELS-P1), wherein the surplus of magnesium stearate sprayed but not used is consecutively recovered. Besides, the amount of magnesium stearate per whole weight of a tablet is determined by an atomic emission spectrometry via measuring the amount of magnesium in the tablet produced.

The mosapride citrate.dihydrate in Table 1 is (±)4-amino-5-chloro-2-ethoxy-N-[[4-(4-fluorobenzyl)-2-morpholinyl] methyl]benzamide citrate-dihydrate, and the compound provided from Dainippon Pharmaceutical Co., Ltd. is used (average particle size: about 3 μm).

The methylcellulose used herein is Metolose SM-25 manufactured by Shin-Etsu Chemical Co., Ltd. [viscosity (of 2% aqueous solution at 20° C.): 25.3 mm$^2$/s (the Japanese Pharmacopoeia)], and the D-mannitol used herein is MANNITOL60 manufactured by ROQUETTE (average particle size 60 μm).

The low-substituted hydroxypropyl cellulose used herein is LH-21 (Shin-Etsu Chemical Co., Ltd.) [average particle size: 37 μm, loose bulk density: 0.34 g/ml, tapped bulk density: 0.60 g/ml, a hydroxypropyl content: 10.9% by weight].

The thaumatin used herein is SAN-SWEET T (San-Ei Gen F. F. I., Inc.), and the sodium glutamate used herein is what is manufactured by AJINOMOTO CO., INC.

The menthol used herein is SAN-FIX MENTHOL No. 25206 (San-Ei Gen F. F. I., Inc.), and the magnesium stearate used herein is what is manufactured by TAIHEI CHEMICALS LIMITED (average particle size: 7.5 μm). The lactose used herein is 200M lactose (DMV International), and the light anhydrous silicic acid used herein is Aerosil (Nippon Aerosil).

Example 1

TABLE 1

Example 1. Formulation

| | Ingredient | Amount (g) | Concentration in final product (% by weight) |
|---|---|---|---|
| Medicament-containing particle | Mosapride citrate•dihydrate | 264.5 | 2.6 |
| | (for mosapride citrate) | (250) | (2.5) |
| | Methylcellulose | 250 | 2.5 |
| | D-Mannitol | 750 | 7.5 |
| Intrabuccally rapidly disintegrating tablet | Medicament-containing particle | 126.45 | 12.6 |
| | D-Mannitol | 793.55 | 79.4 |
| | Low-substituted hydroxypropyl cellulose | 75 | 7.5 |
| | Thaumatin | 1 | 0.1 |
| | Sodium glutamate | 1 | 0.1 |
| | Menthol | 1 | 0.1 |
| | Magnesium stearate | q.s. | 0.2 |

(1) Preparation of a Medicament-Containing Particle

The medicament-containing particle of the invention is prepared according to the above formulation. That is, all the ingredients comprised as a component of the medicament-containing particle are mixed and granulated in an agitating granulator (Powrex Corp., FM-VG-05) while spraying 130 g of purified water, and then dried in a tray type dryer. The resulting granules are sifted by means of a 32 mesh sieve (opening, 500 μm) to give medicament-containing particles whose average particle size is about 250 μm.

(2) Preparation of an Intrabuccally Rapidly Disintegrating Tablet

According to the above formulation, the medicament-containing particle given in (1) and all ingredients of D-mannitol, low-substituted hydroxypropyl cellulose, thaumatin, and sodium glutamate are mixed and granulated in an agitating granulator (Powrex Corp., FM-VG-05) while spraying 140 g of purified water, and then dried in a tray type dryer. The resulting granules are sifted by means of a 22 mesh sieve (opening, 710 μm).

Menthol is mixed with the granules and then the resulting mixture is compressed under a pressure of 100 to 120 MPa/cm$^2$ spraying magnesium stearate with a constant air flow rate of 10 L/min. (Normal) at a supplying rate of about 15 g/h to give tablets (the weight of a tablet is 200 mg and a diameter of 8 mm). The tablets include magnesium stearate whose content is about 0.2% by weight based on the whole weight of a tablet.

Examples 2-12

In a similar manner to Example 1, the medicament-containing particles whose average particle size is about 250 μm and the intrabuccally rapidly disintegrating tablets weight of a tablet is 200 mg), which have the entration shown in Table 3 are prepared based on the ulation in Table 2 shown below.

TABLE 2

Formulation (Amount) (Unit of measurement: g)

| | | Example | | | | | | | | | | |
|---|---|---|---|---|---|---|---|---|---|---|---|---|
| | Ingredient | 2 | 3 | 4 | 5 | 6 | 7 | 8 | 9 | 10 | 11 | 12 |
| Medicament-containing particle | Mosapride citrate•dihydrate | 264.5 | 264.5 | 264.5 | 264.5 | 264.5 | 264.5 | 264.5 | 105.8 | 105.8 | 105.8 | 52.9 |
| | (for mosapride citrate) | (250) | (250) | (250) | (250) | (250) | (250) | (250) | (100) | (100) | (100) | (50) |
| | Methylcellulose | 25 | 50 | 125 | 500 | 1000 | 250 | 250 | 800 | 100 | 100 | 50 |
| | D-Mannitol | 750 | 750 | 750 | 750 | 750 | 500 | 1250 | 300 | 700 | 1000 | 1250 |
| Intrabuccally rapidly disintegrating tablet | Medicament-containing particle | 103.95 | 106.45 | 113.95 | 151.45 | 201.45 | 101.45 | 176.45 | 301.45 | 226.45 | 301.45 | 676.45 |
| | D-Mannitol | 816.05 | 813.55 | 806.05 | 768.55 | 718.55 | 818.55 | 743.55 | 618.55 | 693.55 | 618.55 | 243.55 |
| | Low-substituted hydroxypropyl cellulose | 75 | 75 | 75 | 75 | 75 | 75 | 75 | 75 | 75 | 75 | 75 |
| | Thaumatin | 1 | 1 | 1 | 1 | 1 | 1 | 1 | 1 | 1 | 1 | 1 |
| | Sodium glutamate | 1 | 1 | 1 | 1 | 1 | 1 | 1 | 1 | 1 | 1 | 1 |
| | Menthol | 1 | 1 | 1 | 1 | 1 | 1 | 1 | 1 | 1 | 1 | 1 |
| | Magnesium stearate | q.s. | q.s. | q.s. | q.s. | q.s. | q.s. | q.s. | q.s. | q.s. | q.s. | q.s. |

TABLE 3

Concentration in final product (% by weight)

| | Ingredient | Example 2 | 3 | 4 | 5 | 6 | 7 | 8 | 9 | 10 | 11 | 12 |
|---|---|---|---|---|---|---|---|---|---|---|---|---|
| Medicament-containing particle | Mosapride citrate•dihydrate | 2.6 | 2.6 | 2.6 | 2.6 | 2.6 | 2.6 | 2.6 | 2.6 | 2.6 | 2.6 | 2.6 |
| | (for mosapride citrate) | (2.5) | (2.5) | (2.5) | (2.5) | (2.5) | (2.5) | (2.5) | (2.5) | (2.5) | (2.5) | (2.5) |
| | Methylcellulose | 0.25 | 0.5 | 1.25 | 5 | 10 | 2.5 | 2.5 | 20 | 2.5 | 2.5 | 2.5 |
| | D-Mannitol | 7.5 | 7.5 | 7.5 | 7.5 | 7.5 | 5 | 12.5 | 7.5 | 17.5 | 25 | 62.5 |
| Intrabuccally rapidly disintegrating tablet | Medicament-containing particle | 10.4 | 10.6 | 11.4 | 15.1 | 20.1 | 10.1 | 17.6 | 30.1 | 22.6 | 30.1 | 67.6 |
| | D-Mannitol | 81.6 | 81.4 | 80.6 | 76.9 | 71.9 | 81.9 | 74.4 | 61.9 | 69.4 | 61.9 | 24.4 |
| | Low-substituted hydroxypropyl cellulose | 7.5 | 7.5 | 7.5 | 7.5 | 7.5 | 7.5 | 7.5 | 7.5 | 7.5 | 7.5 | 7.5 |
| | Thaumatin | 0.1 | 0.1 | 0.1 | 0.1 | 0.1 | 0.1 | 0.1 | 0.1 | 0.1 | 0.1 | 0.1 |
| | Sodium glutamate | 0.1 | 0.1 | 0.1 | 0.1 | 0.1 | 0.1 | 0.1 | 0.1 | 0.1 | 0.1 | 0.1 |
| | Menthol | 0.1 | 0.1 | 0.1 | 0.1 | 0.1 | 0.1 | 0.1 | 0.1 | 0.1 | 0.1 | 0.1 |
| | Magnesium stearate | 0.2 | 0.2 | 0.2 | 0.2 | 0.2 | 0.2 | 0.2 | 0.2 | 0.2 | 0.2 | 0.2 |

Examples 13 and 14

In a similar manner to Example 1, the medicament-containing particles and the intrabuccally rapidly disintegrating tablets shown in Table 4 are prepared. However, the tablets of Example 14 are prepared in a versatile mixer (DALTON, 5DM) instead of an agitating granulator while injecting purified water instead of spraying purified water.

TABLE 4

Examples 13 and 14. Formulation

| | | Amount (g) Example | | Concentration in final product (% by weight) Example | |
|---|---|---|---|---|---|
| | Ingredient | 13 | 14 | 13 | 14 |
| Medicament-containing particle | Caffeine | 250 | — | 5 | — |
| | Codeine phosphate | — | 4 | — | 1 |
| | Methylcellulose | 250 | 20 | 5 | 5 |
| | D-Mannitol | 750 | 76 | 15 | 19 |
| | Thaumatin | 5 | 0.2 | 0.1 | 0.05 |
| | Sodium glutamate | 5 | 0.2 | 0.1 | 0.05 |
| Intrabuccally rapidly disintegrating tablet | Medicament-containing particle | 252 | 100.4 | 25.2 | 25.1 |
| | D-Mannitol | 670 | 268 | 67 | 67 |
| | Low-substituted hydroxypropyl cellulose | 75 | 30 | 7.5 | 7.5 |
| | Thaumatin | — | 0.2 | — | 0.05 |
| | Sodium glutamate | — | 0.2 | — | 0.05 |
| | Menthol | 1 | 0.4 | 0.1 | 0.1 |
| | Magnesium stearate | q.s. | q.s. | 0.2 | 0.2 |

Comparative Example 1

In a similar manner to Example 1, the medicament-containing particles whose average particle size is about 250 μm and the intrabuccally rapidly disintegrating tablets shown in Table 5 below are prepared. These tablets are distinguished from the tablets of the present invention because the medicament-containing particles of Comparative Example 1 do not include D-mannitol.

TABLE 5

Comparative Example 1. Formulation

| | Ingredient | Amount (g) | Concentration in final product (% by weight) |
|---|---|---|---|
| Medicament-containing particle | Mosapride citrate•dihydrate | 264.5 | 2.6 |
| | (for mosapride citrate) | (250) | (2.5) |
| | Methylcellulose | 250 | 2.5 |
| | D-Mannitol | — | — |
| Intrabuccally rapidly disintegrating tablet | Medicament-containing particle | 51.45 | 5.1 |
| | D-Mannitol | 868.55 | 86.9 |
| | Low-substituted hydroxypropyl cellulose | 75 | 7.5 |
| | Thaumatin | 1 | 0.1 |
| | Sodium glutamate | 1 | 0.1 |
| | Menthol | 1 | 0.1 |
| | Magnesium stearate | q.s. | 0.2 |

Comparative Example 2

All the ingredients shown in table 6 below except menthol and magnesium stearate are mixed and granulated in an agitating granulator (Powrex Corp., FM-VG-05) while spraying 140 g of purified water, and then dried in a tray type dryer. The resulting granules are sifted by means of a 22 mesh sieve (opening, 710 μm).

These granules are mixed with menthol, and then compressed under a pressure of about 100 to 120 MPa/cm$^2$, spraying magnesium stearate with a constant air flow rate of 10 L/min. (Normal) at a supplying rate of about 15 g/h to provide tablets (each weighing 200 mg and having 8 mm in diameter). The amount of magnesium stearate per the whole weight of a tablet is about 0.2% by weight.

These intrabuccally rapidly disintegrating tablets are the same as the tablets of Example 1 at the viewpoint of the component variety, but the tablets of Comparative Example 2 are distinguished from those of Example 1 because the medicament-containing particles are not prepared in the case of the former.

TABLE 6

Comparative Example 2. Formulation

| Ingredient | Amount (g) | Concentration in final product (% by weight) |
|---|---|---|
| Mosapride citrate•dihydrate | 26.45 | 2.6 |
| (for mosapride citrate) | (25) | (2.5) |
| Methylcellulose | 25 | 2.5 |
| D-Mannitol | 868.55 | 86.9 |
| Low-substituted hydroxypropyl cellulose | 75 | 7.5 |
| Thaumatin | 1 | 0.1 |
| Sodium glutamate | 1 | 0.1 |
| Menthol | 1 | 0.1 |
| Magnesium stearate | q.s. | 0.2 |

Examples 15-24 and Comparative Examples 3-4

In a similar manner to Example 1, the medicament-containing particles whose average particle size is about 100 μm shown in Table 7 below are prepared. Comparative Examples 3 and 4 are distinguished from the present invention because the Comparative Examples do not include methylcellulose.

TABLE 7

Formulation (Amount) (Unit of measurement: g)

| | Ingredient | Example 15 | Example 16 | Example 17 | Example 18 | Example 19 | Comparative Example 3 |
|---|---|---|---|---|---|---|---|
| Medicament-containing particle | Mosapride citrate•dihydrate | 211.6 | 211.6 | 211.6 | 211.6 | 211.6 | 211.6 |
| | (for mosapride citrate) | (200) | (200) | (200) | (200) | (200) | (200) |
| | Methylcellulose | 40 | 100 | 200 | 300 | 400 | — |
| | D-Mannitol | 748.4 | 688.4 | 588.4 | 488.4 | 388.4 | 788.4 |

| | Ingredient | Example 20 | Example 21 | Example 22 | Example 23 | Example 24 | Comparative Example 4 |
|---|---|---|---|---|---|---|---|
| Medicament-containing particle | Mosapride citrate•dihydrate | 105.8 | 105.8 | 105.8 | 105.8 | 105.8 | 105.8 |
| | (for mosapride citrate) | (100) | (100) | (100) | (100) | (100) | (100) |
| | Methylcellulose | 20 | 50 | 100 | 200 | 400 | — |
| | D-Mannitol | 874.2 | 844.2 | 794.2 | 694.2 | 494.2 | 894.2 |

Comparative Examples 5-9

In a similar manner to Example 1, the medicament-containing particles and the intrabuccally rapidly disintegrating tablets shown in Table 9 below are prepared based on the formulation in Table 8 shown below. These medicament-containing particles are distinguished from those of Example 1 because each of the particles of the former include the other water-soluble polymer instead of methylcellulose and additionally the average particle size of the former is about 150 μm.

The pullulan used herein is Pullulan PI-20 (Hayashibara Shoji Inc.), the polyvinyl alcohol (PVA) used herein is Shin-etsu Poval (Shin-Etsu Chemical Co., Ltd.). The hydroxypropyl cellulose (HPC) used herein is HPC L (NIPPON SODA CO., LTD.), the hydroxypropylmethylcellulose (HPMC) used herein is TC-5RW (Shin-Etsu Chemical Co., Ltd.), and the polyvinylpyrrolidone (PVP) used herein is Povidone K-30 (ISP).

TABLE 8

Formulation (Amount) (Unit of measurement: g)

| | | Comparative Example | | | | |
|---|---|---|---|---|---|---|
| | Ingredient | 5 | 6 | 7 | 8 | 9 |
| Medicament-containing particle | Mosapride citrate•dihydrate | 264.5 | 264.5 | 264.5 | 264.5 | 264.5 |
| | (for mosapride citrate) | (250) | (250) | (250) | (250) | (250) |
| | Pullulan | 250 | — | — | — | — |
| | Polyvinyl alcohol | — | 250 | — | — | — |
| | Hydroxypropyl cellulose | — | — | 250 | — | — |
| | hydroxypropylmethyl cellulose | — | — | — | 250 | — |
| | Polyvinylpyrrolidone | — | — | — | — | 250 |
| | D-Mannitol | 750 | 750 | 750 | 750 | 750 |
| Intrabuccally rapidly disintegrating tablet | Medicament-containing particle | 126.45 | 126.45 | 126.45 | 126.45 | 126.45 |
| | D-Mannitol | 793.55 | 793.55 | 793.55 | 793.55 | 793.55 |
| | Low-substituted hydroxypropyl cellulose | 75 | 75 | 75 | 75 | 75 |
| | Thaumatin | 1 | 1 | 1 | 1 | 1 |
| | Sodium glutamate | 1 | 1 | 1 | 1 | 1 |
| | Menthol | 1 | 1 | 1 | 1 | 1 |
| | Magnesium stearate | q.s. | q.s. | q.s. | q.s. | q.s. |

TABLE 9

Concentration in final product (% by weight)

| | | Comparative Example | | | | |
|---|---|---|---|---|---|---|
| | Ingredient | 5 | 6 | 7 | 8 | 9 |
| Medicament-containing particle | Mosapride citrate•dihydrate | 2.6 | 2.6 | 2.6 | 2.6 | 2.6 |
| | (for mosapride citrate) | (2.5) | (2.5) | (2.5) | (2.5) | (2.5) |
| | Pullulan | 2.5 | — | — | — | — |
| | Polyvinyl alcohol | — | 2.5 | — | — | — |
| | Hydroxypropyl cellulose | — | — | 2.5 | — | — |
| | hydroxypropyl-methylcellulose | — | — | — | 2.5 | — |
| | Polyvinyl-pyrrolidone | — | — | — | — | 2.5 |
| | D-Mannitol | 7.5 | 7.5 | 7.5 | 7.5 | 7.5 |
| Intrabuccally rapidly disintegrating tablet | Medicament-containing particle | 12.6 | 12.6 | 12.6 | 12.6 | 12.6 |
| | D-Mannitol | 79.4 | 79.4 | 79.4 | 79.4 | 79.4 |
| | Low-substituted hydroxypropyl cellulose | 7.5 | 7.5 | 7.5 | 7.5 | 7.5 |
| | Thaumatin | 0.1 | 0.1 | 0.1 | 0.1 | 0.1 |
| | Sodium glutamate | 0.1 | 0.1 | 0.1 | 0.1 | 0.1 |
| | Menthol | 0.1 | 0.1 | 0.1 | 0.1 | 0.1 |
| | Magnesium stearate | 0.2 | 0.2 | 0.2 | 0.2 | 0.2 |

Example 25 and Comparative Examples 10-17

In a similar manner to Example 1, the medicament-containing particles and the intrabuccally rapidly disintegrating tablets shown in Table 11 below are prepared based on the formulation in Table 10 shown below. These medicament-containing particles are distinguished from those of Example 1 because the average particle size of the former is about 150 μm, and the medicament-containing particles in each Comparative Example are distinguished from those of Example 25 because the former includes the other sugar or sugar alcohol instead of mannitol.

The xylitol used herein is Xylit (Towa Chemical Industry Co., Ltd.), and the trehalose used herein is Trehalose P (Asahi KASEI Corporation). The erythritol used herein is Erythritol micro powder (Nikken Chemicals Co., Ltd), the sorbitol used herein is D-sorbitol DP-50 (Towa Chemical Industry Co., Ltd.), and the maltitol used herein is Amalty (Towa Chemical Industry Co., Ltd.). The lactose used herein is 200M lactose (DMV International), the lactitol used herein is Milchen (Towa Chemical Industry Co., Ltd.), and the sucrose used herein is High Grade Powder Sugar (Nissin Sugar Manufacturing Co., Ltd.).

TABLE 10

Formulation (Amount) (Unit of measurement: g)

| | | Example | Comparative Example | | | | | | | |
|---|---|---|---|---|---|---|---|---|---|---|
| | Ingredient | 25 | 10 | 11 | 12 | 13 | 14 | 15 | 16 | 17 |
| Medicament-containing particle | Mosapride citrate•dihydrate | 264.5 | 264.5 | 264.5 | 264.5 | 264.5 | 264.5 | 264.5 | 264.5 | 264.5 |
| | (for mosapride citrate) | (250) | (250) | (250) | (250) | (250) | (250) | (250) | (250) | (250) |
| | Methylcellulose | 250 | 250 | 250 | 250 | 250 | 250 | 250 | 250 | 250 |
| | D-Mannitol | 750 | — | — | — | — | — | — | — | — |
| | Xylitol | — | 750 | — | — | — | — | — | — | — |
| | Trehalose | — | — | 750 | — | — | — | — | — | — |
| | Erythritol | — | — | — | 750 | — | — | — | — | — |
| | Sorbitol | — | — | — | — | 750 | — | — | — | — |

TABLE 10-continued

Formulation (Amount) (Unit of measurement: g)

|  | Ingredient | Example 25 | Comparative Example 10 | 11 | 12 | 13 | 14 | 15 | 16 | 17 |
|---|---|---|---|---|---|---|---|---|---|---|
|  | Maltitol | — | — | — | — | — | 750 | — | — | — |
|  | Lactose | — | — | — | — | — | — | 750 | — | — |
|  | Lactitol | — | — | — | — | — | — | — | 750 | — |
|  | Sucrose | — | — | — | — | — | — | — | — | 750 |
| Intrabuccally rapidly disintegrating tablet | Medicament-containing particle | 126.45 | 126.45 | 126.45 | 126.45 | 126.45 | 126.45 | 126.45 | 126.45 | 126.45 |
|  | D-Mannitol | 793.55 | 793.55 | 793.55 | 793.55 | 793.55 | 793.55 | 793.55 | 793.55 | 793.55 |
|  | Low-substituted hydroxypropyl cellulose | 75 | 75 | 75 | 75 | 75 | 75 | 75 | 75 | 75 |
|  | Thaumatin | 1 | 1 | 1 | 1 | 1 | 1 | 1 | 1 | 1 |
|  | Sodium glutamate | 1 | 1 | 1 | 1 | 1 | 1 | 1 | 1 | 1 |
|  | Menthol | 1 | 1 | 1 | 1 | 1 | 1 | 1 | 1 | 1 |
|  | Magnesium stearate | q.s. | q.s. | q.s. | q.s. | q.s. | q.s. | q.s. | q.s. | q.s. |

TABLE 11

Concentration in final product

|  | Ingredient | Example 25 | Comparative Example 10 | 11 | 12 | 13 | 14 | 15 | 16 | 17 |
|---|---|---|---|---|---|---|---|---|---|---|
| Medicament-containing particle | Mosapride citrate·dihydrate | 2.6 | 2.6 | 2.6 | 2.6 | 2.6 | 2.6 | 2.6 | 2.6 | 2.6 |
|  | (for mosapride citrate) | (2.5) | (2.5) | (2.5) | (2.5) | (2.5) | (2.5) | (2.5) | (2.5) | (2.5) |
|  | Methylcellulose | 2.5 | 2.5 | 2.5 | 2.5 | 2.5 | 2.5 | 2.5 | 2.5 | 2.5 |
|  | D-Mannitol | 7.5 | — | — | — | — | — | — | — | — |
|  | Xylitol | — | 7.5 | — | — | — | — | — | — | — |
|  | Trehalose | — | — | 7.5 | — | — | — | — | — | — |
|  | Erythritol | — | — | — | 7.5 | — | — | — | — | — |
|  | Sorbitol | — | — | — | — | 7.5 | — | — | — | — |
|  | Maltitol | — | — | — | — | — | 7.5 | — | — | — |
|  | Lactose | — | — | — | — | — | — | 7.5 | — | — |
|  | Lactitol | — | — | — | — | — | — | — | 7.5 | — |
|  | Sucrose | — | — | — | — | — | — | — | — | 7.5 |
| Intrabuccally rapidly disintegrating tablet | Medicament-containing particle | 12.6 | 12.6 | 12.6 | 12.6 | 12.6 | 12.6 | 12.6 | 12.6 | 12.6 |
|  | D-Mannitol | 79.4 | 79.4 | 79.4 | 79.4 | 79.4 | 79.4 | 79.4 | 79.4 | 79.4 |
|  | Low-substituted hydroxypropyl cellulose | 7.5 | 7.5 | 7.5 | 7.5 | 7.5 | 7.5 | 7.5 | 7.5 | 7.5 |
|  | Thaumatin | 0.1 | 0.1 | 0.1 | 0.1 | 0.1 | 0.1 | 0.1 | 0.1 | 0.1 |
|  | Sodium glutamate | 0.1 | 0.1 | 0.1 | 0.1 | 0.1 | 0.1 | 0.1 | 0.1 | 0.1 |
|  | Menthol | 0.1 | 0.1 | 0.1 | 0.1 | 0.1 | 0.1 | 0.1 | 0.1 | 0.1 |
|  | Magnesium stearate | 0.2 | 0.2 | 0.2 | 0.2 | 0.2 | 0.2 | 0.2 | 0.2 | 0.2 |

Examples 26 and 27

In a similar manner to Example 1, the medicament-containing particles and the intrabuccally rapidly disintegrating tablets shown in Table 12 below are prepared. The medicament-containing particles are not sifted but milled by a pulverizer (HOSOKAWAMICRON CORPORATION, AP-S). The average particle size is about 25 μm.

TABLE 12

Examples 26 and 27. Formulation

|  |  | Amount (g) Example |  | Concentration in final product (% by weight) Example |  |
|---|---|---|---|---|---|
|  | Ingredient | 26 | 27 | 26 | 27 |
| Medicament-containing particle | Mosapride citrate·dihydrate | 211.6 | 105.8 | 2.6 | 2.6 |
|  | (for mosapride citrate) | (200) | (100) | (2.5) | (2.5) |
|  | Methylcellulose | 200 | 200 | 2.5 | 5 |
|  | D-Mannitol | 588.4 | 694.2 | 7.4 | 17.4 |
| Intrabuccally rapidly disintegrating tablet | Medicament-containing particle | 125 | 250 | 12.5 | 25 |
|  | D-Mannitol | 796 | 671 | 79.6 | 67.1 |
|  | Low-substituted hydroxypropyl cellulose | 75 | 75 | 7.5 | 7.5 |
|  | Thaumatin | 1 | 1 | 0.1 | 0.1 |
|  | Menthol | 1 | 1 | 0.1 | 0.1 |
|  | Magnesium stearate | q.s. | q.s. | 0.2 | 0.2 |

Experiment 1

The profiles of the medicament-containing particles and the tablets prepared in each Example and each Comparative Example were tested and the results were shown in Table 13-15. The medicament-containing particles were evaluated as to a masking degree of the unpleasant taste; and the tablets were evaluated as to a disintegration time, a tensile strength, a masking degree of the unpleasant taste, a feeling in buccal cavity when administered, and a dissolution test. In addition, time-dependent changes of the dissolution tests with the tablets of Example 1 and Comparative Example 1 are shown in FIG. 1.

TABLE 13

| Example and Comparative Example | | Medicament-containing particle Masking degree of the unpleasant taste*1 | Tablets | | | | | |
|---|---|---|---|---|---|---|---|---|
| | | | Disintegration time (sec.) | | Tensile strength*4 (N/cm²) | Masking degree of the unpleasant taste*1 | feeling in a buccal cavity when administered*5 | Dissolution Test*6 |
| | | | Japanese Pharmacopoeia*2 | In buccal cavity*3 | | | | |
| Example | 1 | ◎ | 14 | 17 | 162 | ◎ | — | ○ |
| | 2 | Δ | 13 | 15 | 118 | ○ | — | ○ |
| | 3 | Δ | 13 | 17 | 128 | ○ | — | ○ |
| | 4 | ○ | 15 | 20 | 175 | ◎ | — | ○ |
| | 5 | ◎ | 13 | 18 | 133 | ◎ | — | ○ |
| | 6 | ◎ | 13 | 27 | 159 | ◎ | — | ○ |
| | 7 | ◎ | 14 | 22 | 146 | ◎ | — | ○ |
| | 8 | ◎ | 13 | 16 | 164 | ◎ | — | ○ |
| | 9 | ○ | 24 | 39 | 131 | ○ | — | ○ |
| | 10 | ◎ | 17 | 23 | 143 | ◎ | — | ○ |
| | 11 | ○ | 17 | 23 | 146 | ◎ | — | ○ |
| | 12 | Δ | 17 | 25 | 141 | ○ | — | ○ |
| | 13 | Δ | 20 | 34 | 177 | ○ | — | ○ |
| | 14 | Δ | 19 | 36 | 154 | ○ | — | ○ |
| Comparative Example | 1 | XX | 15 | 15 | 141 | X | — | X |
| | 2 | | 16 | 25 | 148 | X | — | ○ |

*¹Masking degree of the unpleasant taste (compared with the medicament) after setting the preparation on each tongue of three healthy adult men selected as a subject and disintegrating the preparation with his mouth closed and without chewing (the worst score is shown as a result). ◎: Masking effect was clearly exhibited and the unpleasant taste was not felt at all. ○: Masking effect was exhibited, and the unpleasant taste was almost masked and was not actually felt. Δ: Masking effect was exhibited and the unpleasant taste was not almost felt. X: Masking effect was somewhat exhibited, but the unpleasant taste was felt. XX: There was no masking effect and the unpleasant taste was felt.
*²The disintegration test of the Japanese Pharmacopoeia XIV (condition: without auxiliary disks).
*³The time that the tablet is disintegrated when the tablet was set on each tongue of three healthy adult men selected as a subject and his mouth was closed without chewing (the longest time is shown as a result).
*⁴The tensile strength was calculated through the following formula with a breaking load obtained using a tablet hardness tester (SCHLEUNIGER).
Tensile strength (N/cm²) = 2 × Rupture load (N)/(π × Diameter of the tablet (cm) × Thickness of the tablet (cm)) wherein π means circular constant.
*⁵Feeling in buccal cavity when administered. +: Sandy −: Not sandy
*⁶○ means the dissolution of 85% or more in substance after 15 minutes according to the dissolution test described in the Japanese Pharmacopoeia XIV [using paddle method, 50 rpm, resolution medium: 900 mL of water at 37° C.]; and X means the dissolution of less than 85%.

TABLE 14

| Example and Comparative Example | | Medicament-containing particle Masking degree of the unpleasant taste*1 |
|---|---|---|
| Example | 15 | Δ |
| | 16 | ○ |
| | 17 | ◎ |
| | 18 | ◎ |
| | 19 | ◎ |
| | 20 | Δ |
| | 21 | Δ |
| | 22 | ○ |
| | 23 | ◎ |
| | 24 | ◎ |
| Comparative Example | 3 | XX |
| | 4 | XX |

*¹Masking degree of the unpleasant taste (compared with the medicament) after setting the preparation on each tongue of three healthy adult men selected as a subject and disintegrating the preparation with his mouth closed and without chewing (the worst score is shown as a result).
◎: Masking effect was clearly exhibited and the unpleasant taste was not felt at all.
○: Masking effect was exhibited, and the unpleasant taste was almost masked and was not actually felt.
Δ: Masking effect was exhibited and the unpleasant taste was not almost felt.
X: Masking effect was somewhat exhibited, but the unpleasant taste was felt.
XX: There was no masking effect and the unpleasant taste was felt.

TABLE 15

| Example and Comparative Example | | Medicament-containing particle Masking degree of the unpleasant taste*1 | Tablet Masking degree of the unpleasant taste*1 | Tablet feeling in buccal cavity when administered*2 | Dissolution Test*3 |
|---|---|---|---|---|---|
| Example | 25 | ⊚ | ⊚ | — | ○ |
| Comparative Example | 5 | XX | X | — | ○ |
| | 6 | XX | X | — | ○ |
| | 7 | XX | X | — | ○ |
| | 8 | XX | X | — | ○ |
| | 9 | XX | X | — | ○ |
| | 10 | X | X | — | ○ |
| | 11 | X | X | — | ○ |
| | 12 | XX | X | — | ○ |
| | 13 | X | X | — | ○ |
| | 14 | X | X | — | ○ |
| | 15 | XX | X | — | ○ |
| | 16 | XX | X | — | ○ |
| | 17 | XX | X | — | ○ |
| Example | 26 | ⊚ | ⊚ | — | ○ |
| | 27 | ⊚ | ⊚ | — | ○ |

*1 Masking degree of the unpleasant taste (compared with the medicament) after setting the preparation on each tongue of three healthy adult men selected as a subject and disintegrating the preparation with his mouth closed and without chewing (the worst score is shown as a result).
⊚: Masking effect was clearly exhibited and the unpleasant taste was not felt at all.
○: Masking effect was exhibited, and the unpleasant taste was almost masked and was not actually felt.
Δ: Masking effect was exhibited and the unpleasant taste was not almost felt.
X: Masking effect was somewhat exhibited, but the unpleasant taste was felt.
XX: There was no masking effect and the unpleasant taste was felt.
*2 Feeling in buccal cavity when administered.
+: Sandy
−: Not sandy
*3 ○ means the dissolution of 85% or more in substance after 15 minutes according to the dissolution test described in the Japanese Pharmacopoeia XIV [using paddle method, 50 rpm, resolution medium: 900 mL of water at 37° C.]; and X means the dissolution of less than 85%.

Examples 28 and 29

According to the following formulation shown in Table 16, intrabuccally rapidly disintegrating powders (fine granules) (Example 28) and intrabuccally rapidly disintegrating granules (Example 29) are prepared. With regard to fine granules, in detail, medicament-containing particles whose average particle size is about 250 μm are prepared in a similar manner to Example 1, and the resulting medicament-containing particles and all ingredients of D-mannitol, low-substituted hydroxypropyl cellulose, and light anhydrous silicic acid are mixed and granulated in an agitating granulator (Powrex Corp., FM-VG-05) while spraying 150 g of purified water, and then dried in a tray type dryer. The resulting granules are sifted by means of a 32 mesh sieve (opening, 500 μm).

With regard to intrabuccally disintegrating granules, the medicament-containing particles obtained in the same manner as the above procedure and all ingredients of D-mannitol, low-substituted hydroxypropyl cellulose, light anhydrous silicic acid, and hydroxypropyl cellulose are mixed and granulated in an agitating granulator (Powrex Corp., FM-VG-05) spraying 100 g of purified water, furthermore granulated by extrusion with a tabletop granulator (Tsutsui Rikagaku Kikai Co., Ltd, KAR-180, diameter of screen: 1.0 mm), and then dried in a tray type dryer. The resulting granules are sifted by means of a 16 mesh sieve (opening, 1000 μm).

TABLE 16

Examples 28 and 29. Formulation

| | Ingredient | Amount (g) Example 28 | Amount (g) Example 29 | Concentration in final product (% by weight) Example 28 | Concentration in final product (% by weight) Example 29 |
|---|---|---|---|---|---|
| Medicament-containing particle | Mosapride citrate·dihydrate (for mosapride citrate) | 105.8 (100) | 105.8 (100) | 2.6 (2.5) | 2.6 (2.5) |
| | Methylcellulose | 200 | 200 | 5 | 5 |
| | D-Mannitol | 694.2 | 694.2 | 17.4 | 17.4 |
| Preparation | Medicament-containing particle | 250 | 250 | 25 | 25 |
| | D-Mannitol | 670 | 665 | 67 | 66.5 |
| | Low-substituted hydroxypropyl cellulose | 75 | 75 | 7.5 | 7.5 |
| | Hydroxypropyl cellulose | — | 5 | — | 0.5 |
| | Light anhydrous silicic acid | 5 | 5 | 0.5 | 0.5 |

Experiment 2

In a similar manner to Experiment 1, a masking degree of the unpleasant taste of the preparations in Examples 28 and 29 was evaluated. The results are shown in Table 17.

TABLE 17

| Example | | Masking degree of the unpleasent taste*[1] |
|---|---|---|
| Example | 28 | ⊚ |
| | 29 | ⊚ |

*[1]Masking degree of the unpleasant taste (compared with the medicament) after setting the preparation on each tongue of three healthy adult men selected as a subject and disintegrating the preparation with his mouth closed and without chewing.
⊚: Masking effect was clearly exhibited and the unpleasant taste was not felt at all.
○: Masking effect was exhibited, and the unpleasant taste was almost masked and was not actually felt.
△: Masking effect was exhibited and the unpleasant taste was not almost felt.
X: Masking effect was somewhat exhibited, but the unpleasant taste was felt.
XX: There was no masking effect and the unpleasant taste was felt.

Example 30

The tablets are prepared according to the formulation described in Table 18 below. That is, as a similar procedure in Example 1, medicament-containing particles whose average particle size is about 250 μm are prepared, and then the resulting medicament-containing particles and all ingredients of lactose, low-substituted hydroxypropyl cellulose, and light anhydrous silicic acid are mixed and granulated in a fluid bed granulating machine (Freund Industrial Co., Ltd., FLO-5) while spraying a solution of hydroxypropyl cellulose in 380 g of purified water, and dried. The resulting granules are sifted by means of a 22 mesh sieve (opening, 710 μm). Thereto magnesium stearate is added, and the resulting mixture is mixed by a V-BLENDER (Fuji Paudal Co., Ltd., VM-5) and compressed under a pressure of about 200 MPa/cm² to provide tablets (each weighing 200 mg and having 8 mm in diameter).

TABLE 18

| Example 30. Formulation | | | | |
|---|---|---|---|---|
| | Ingredient | | Amount (g) | Concentration in final product (% by weight) |
| Medicament-containing particle | Mosapride citrate•dihydrate (for mosapride citrate) | | 105.8 (100) | 2.6 (2.5) |
| | Methylcellulose | | 200 | 5 |

TABLE 18-continued

| Example 30. Formulation | | | |
|---|---|---|---|
| | Ingredient | Amount (g) | Concentration in final product (% by weight) |
| Plain tablet | D-Mannitol | 694.2 | 17.4 |
| | Medicament-containing particle | 250 | 25 |
| | Lactose | 615 | 61.5 |
| | Low-susbstituted hydroxypropyl cellulose | 100 | 10 |
| | Hydroxypropyl cellulose | 20 | 2 |
| | Light anhydrous silicic acid | 5 | 0.5 |
| | Magnesium stearate | 10 | 1 |

Examples 31-33

The powders (Example 31), the powders (fine granules) (Example 32) and the granules (Example 33) are prepared based on the formulation shown in Table 19. With regard to all types of the preparations, medicament-containing particles whose average particle size is about 250 μm are prepared in a similar manner to Example 1. With regard to the powders (Example 31), all ingredients of the obtained medicament-containing particle, lactose, and light anhydrous silicic acid are mixed by a V-BLENDER (Fuji Paudal Co., Ltd., VM-10) and sifted by means of a 22 mesh sieve (opening: 710 μm).

With regard to the powders (fine granules) (Example 32), the obtained medicament-containing particles and all ingredients of lactose, light anhydrous silicic acid and hydroxypropyl cellulose are mixed and granulated in an agitating granulator (Powrex Corp., FM-VG-05) while spraying 150 g of purified water, and then dried in a tray type dryer. The resulting granules are sifted by means of a 32 mesh sieve (opening, 500 μm).

With regard to the granule (Example 33), the obtained medicament-containing particles and all ingredients of lactose, light anhydrous silicic acid and hydroxypropyl cellulose are mixed and granulated in an agitating granulator (Powrex Corp., FM-VG-05) while spraying 100 g of purified water, furthermore granulated by extrusion with a tabletop granulator (Tsutsui Rikagaku Kikai Co., Ltd, KAR-180, diameter of screen: 1.0 mm), and then dried in a tray type dryer. The resulting granules are sifted by means of a 16 mesh sieve (opening, 1000 μm).

TABLE 19

| Examples 31-33. Formulation | | | | | | | |
|---|---|---|---|---|---|---|---|
| | | Amount (g) Example | | | Concentration in final product (% by weight) Example | | |
| | Ingredient | 31 | 32 | 33 | 31 | 32 | 33 |
| Medicament-containing particle | Mosapride citrate•dihydrate | 105.8 | 105.8 | 105.8 | 2.6 | 2.6 | 2.6 |
| | (for mosapride citrate) | (100) | (100) | (100) | (2.5) | (2.5) | (2.5) |
| | Methylcellulose | 200 | 200 | 200 | 5 | 5 | 5 |
| preparation | D-Mannitol | 694.2 | 694.2 | 694.2 | 17.4 | 17.4 | 17.4 |
| | Medicament-containing particle | 250 | 250 | 250 | 25 | 25 | 25 |
| | Lactose | 745 | 715 | 725 | 74.5 | 71.5 | 72.5 |
| | Hydroxypropyl cellulose | — | 30 | 20 | — | 3 | 2 |
| | Light anhydrous silicic acid | 5 | 5 | 5 | 0.5 | 0.5 | 0.5 |

Experiment 3

In a similar manner to Experiment 1, a masking degree of the unpleasant taste of the preparations in Examples 30-33 was evaluated. The results are shown in Table 20.

TABLE 20

| Example | Masking degree of the unpleasant taste*[1] | |
| --- | --- | --- |
| | After holding for 30 sec. | After taking the tablet |
| 30 | ⊚ | ⊚ |
| 31 | ⊚ | ⊚ |
| 32 | ⊚ | ⊚ |
| 33 | ⊚ | ⊚ |

*[1]Masking degree of the unpleasant taste after setting the preparation on each tongue of three healthy adult men selected as a subject, closing his mouth and holding for 30 minutes; and masking degree of the unpleasant taste in his mouth after taking the preparation with 100 mL of water posterior to the holding (compared with the medicament).
⊚: Masking effect was clearly exhibited and the unpleasant taste was not felt at all.
○: Masking effect was exhibited, and the unpleasant taste was almost masked and was not actually felt.
Δ: Masking effect was exhibited and the unpleasant taste was not almost felt.
X: Masking effect was somewhat exhibited, but the unpleasant taste was felt.
XX: There was no masking effect and the unpleasant taste was felt.

INDUSTRIAL APPLICABILITY

The medicament-containing particle of the invention can be the bitter taste of the medicament alleviated, and the preparation containing the particle can make the unpleasant taste masked and can make the rapid-solubility possible.

The invention claimed is:

1. A medicament-containing particle wherein an unpleasant taste of the medicament is masked, which is obtained by mixing and granulating a composition consisting essentially of the following ingredients:
   (1) the medicament with an unpleasant taste,
   (2) methylcellulose, and
   (3) mannitol,
   wherein the amount of the methylcellulose is 0.8 to 5 parts by weight per 1 part by weight of the medicament with an unpleasant taste, the amount of the mannitol is 0.3 to 12 parts by weight per 1 part by weight of the methylcellulose, and wherein the methylcellulose does not overall cover over the medicament, and a part of the medicament exists on the surface of the particle, and the unpleasant taste of the medicament was not felt at all.

2. The medicament-containing particle according to claim 1 wherein the amount of the mannitol is 0.5 to 12 parts by weight per 1 part by weight of the methylcellulose.

3. The medicament-containing particle according to claim 1 wherein the amount of the mannitol is 0.7 to 7.5 parts by weight per 1 part by weight of the methylcellulose.

4. The medicament-containing particle according to claim 1 wherein the mannitol is D-mannitol.

5. The medicament-containing particle according to claim 1 wherein the medicament with an unpleasant taste is 4-amino-5-chloro-2-ethoxy-N-[[4-(4-fluorobenzyl)-2-morpholinyl]methyl]benzamide or a pharmaceutically acceptable salt thereof.

6. The medicament-containing particle according to claim 1 which is obtained by mixing and granulating a composition consisting essentially of the following ingredients:
   (1) (±)-4-amino-5-chloro-2-ethoxy-N-[[4-(4-fluorobenzyl)-2-morpholinyl]methyl]benzamide citrate dihydrate as a medicament,
   (2) methylcellulose, and
   (3) D-mannitol,
   wherein the amount of the methylcellulose is about 0.8 to about 10 parts by weight per 1 part by weight of (±)-4-amino-5-chloro-2-ethoxy-N-[[4-(4-fluorobenzyl)-2-morpholinyl]-methyl]benzamide citrate, and
   the amount of the D-marmitol is about 0.5 to about 12 parts by weight per 1 part by weight of the methylcellulose.

7. A solid pharmaceutical preparation comprising the medicament-containing particle set forth in claim 1 and other pharmaceutically acceptable ingredients.

8. The solid pharmaceutical preparation according to claim 7 wherein the solid preparation is in the form of a tablet or a pill.

9. The solid pharmaceutical preparation according to claim 7 wherein the solid preparation is in the form of a granule, a fine granule or a powder.

10. The solid pharmaceutical preparation according to claim 7 which is an intrabuccally rapidly disintegrating preparation.

11. The solid pharmaceutical preparation according to claim 10 wherein the intrabuccally rapidly disintegrating preparation is in the form of a tablet.

12. The solid pharmaceutical preparation according to claim 10 wherein the intrabuccally rapidly disintegrating preparation is in the form of a granule, a fine granule, or a powder.

13. The intrabuccally rapidly disintegrating preparation set forth in claim 10 which is characterized by the following properties:
   (i) disintegrating within 40 seconds on a tongue of a healthy adult with his mouth closed and without chewing,
   (ii) dissolving at a substantial dissolution rate of 85% or more after 15 minutes according to the dissolution test described in the Japanese Pharmacopoeia XIV [using Method 2 (50 rpm) for tablets or Method 1 (50 rpm) for the form of a granule, a fine granule, or a powder, resolution medium: 900 mL of water], and
   (iii) not producing an unpleasant taste on setting the preparation in buccal cavity.

14. A process for preparing a medicament-containing particle wherein an unpleasant taste of the medicament is masked and not felt at all, comprising mixing and granulating a composition consisting essentially of the following ingredients, with water: (1) the medicament with an unpleasant taste, (2) methylcellulose whose amount is 0.8 to 10 parts by weight per 1 part by weight of the medicament with an unpleasant taste and (3) mannitol whose amount is 0.3 to 12 parts by weight per 1 part by weight of the methylcellulose, to obtain a particle wherein the methylcellulose does not overall cover over the medicament, and a part of the medicament exists on the surface of the particle.

15. A commercial package which comprises the solid preparation set forth in claim 7 comprising 4-amino-5-chloro-2-ethoxy-N-[[4-(4-fluorobenzyl)-2-morpholinyl]methyl]benzamide or a pharmaceutically acceptable salt thereof as a medicament with an unpleasant taste; and a written matter as to the solid preparation,
   including a description on the outside of the package or in the written matter inside the package which states that the solid preparation is used for promoting gastrointestinal motility, improving postgastrectomy condition, or treating gastroesophageal reflux disease (GERD).

16. The medicament-containing particle according to claim 1 wherein the composition further consists of a binder.

17. The process according to claim 14 wherein the composition further consists of a binder.

18. The solid preparation according to claim 7 wherein the medicament-containing particle further consists of a binder.

19. A medicament-containing particle wherein an unpleasant taste of the medicament is masked, which is obtained by mixing and granulating a composition consisting of the following ingredients:
(1) a medicament with an unpleasant taste,
(2) methylcellulose, and
(3) mannitol wherein the amount methylcellulose is 0.8 to 5 parts by weight per 1 part by weight of the medicament with an unpleasant taste, the amount of the mannitol is 0.3 to 12 parts by weight per 1 part by weight of the methylcellulose, and wherein the methylcellulose does not overall cover over the medicament, and a part of the medicament exists on the surface of the particle, and the unpleasant taste of the medicament was not felt at all.

20. A medicament-containing particle wherein an unpleasant taste of the medicament is masked, which is obtained by mixing and granulating a composition consisting of the following ingredients:
(1) a medicament with an unpleasant taste,
(2) methylcellulose,
(3) mannitol, and
(4) a binder and/or fluidization agent wherein the amount of the methylcellulose is 0.8 to 5 parts by weight per 1 part by weight of the medicament with an unpleasant taste, the amount of the mannitol is 0.3 to 12 parts by weight per 1 part by weight of the methylcellulose and wherein the methylcellulose does not overall cover over the medicament, and a part of the medicament exists on the surface of the particle, and the unpleasant taste of the medicament was not felt at all.

21. A medicament-containing particle wherein an unpleasant taste of the medicament is masked, which is obtained by mixing and granulating a composition consisting of the following ingredients:
(1) a medicament with an unpleasant taste,
(2) methylcellulose,
(3) mannitol, and
(4) 1 to 4 ingredients selected from the group consisting of a binder, a fluidization agent, a corrigent and a disintegrant, wherein the corrigent is one or more selected from the group consisting of neotame, thaumatin, aspartame, stevia, saccharin sodium, and sodium glutamate wherein the amount of the methylcellulose is 0.8 to 5 parts by weight per 1 part by weight of the medicament with an unpleasant taste, the amount of the mannitol is 0.3 to 12 parts by weight per 1 part by weight of the methylcellulose, and wherein the methylcellulose does not overall cover over the medicament, and a part of the medicament exists on the surface of the particle, and the unpleasant taste of the medicament was not felt at all.

* * * * *